United States Patent [19]

Gätzi

[11] 4,100,290
[45] Jul. 11, 1978

[54] PYRIDINE-4-CARBOXYLIC ACID HYDRAZONES FOR COMBATTING PHYTOPATHOGENIC MICROORGANISMS

[75] Inventor: Karl Gätzi, Basel, Switzerland

[73] Assignee: Ciba-Geigy Corporation, Ardsley, N.Y.

[21] Appl. No.: 749,863

[22] Filed: Dec. 13, 1976

Related U.S. Application Data

[63] Continuation-in-part of Ser. No. 685,594, May 12, 1976, abandoned.

[30] Foreign Application Priority Data

May 14, 1975 [CH] Switzerland .................. 06192/75
Apr. 2, 1976 [CH] Switzerland .................. 04148/76

[51] Int. Cl.² .................. A61K 31/455; C07D 213.86
[52] U.S. Cl. .................. 424/266; 260/295.5 H; 260/295 H; 542/418
[58] Field of Search .................. 260/295 H, 295.5 H; 424/266; 542/416, 417, 418

[56] References Cited

U.S. PATENT DOCUMENTS

2,703,322  3/1955  Fox .................. 260/295.5
2,855,400  10/1958  Gutmann et al. .................. 260/295 H

OTHER PUBLICATIONS

Proinov, Chem. Abstracts, vol. 84, p. 378, parag. 147901p, (1973).
Parravicini et al., Chem. Abstracts, vol. 84, p. 30831, parag. 30825z, (1976).

*Primary Examiner*—Natalie Trousof
*Assistant Examiner*—Cary Owens
*Attorney, Agent, or Firm*—Harry Falber

[57] ABSTRACT

Compounds of formula I

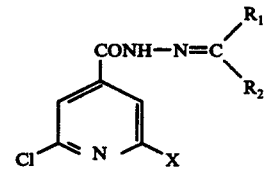

wherein
X represents chlorine, methyl of methoxy
$R_1$ represents hydrogen or $C_1$-$C_6$-alkyl, and
$R_2$ represents $C_1$-$C_6$-alkyl, $C_3$-$C_4$-alkenyl, alkyl($C_1$-$C_4$)-carbonyl or phenyl, or
$R_1$ and $R_2$ together represent a $C_4$-$C_6$-alkylene chain,
whereby the total number of carbon atoms of the radicals $R_1$ and $R_2$ is three or more as well as the salts thereof with organic and inorganic acids which are active against phytopathogenic microorganisms.

28 Claims, No Drawings

PYRIDINE-4-CARBOXYLIC ACID HYDRAZONES FOR COMBATTING PHYTOPATHOGENIC MICROORGANISMS

CROSS REFERENCE

This application is a continuation in part of Ser. No. 685,594, filed May 12, 1976, and which is now abandoned.

The present invention relates to pyridine-4-carboxylic acid hydrazones, as well as to compositions and processes for combatting phytopathogenic microorganisms.

The compounds of the invention correspond to formula I

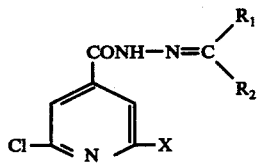

wherein

X represents chlorine, methyl or methoxy, and $R_1$ represents hydrogen or $C_1$-$C_6$-alkyl and $R_2$ represents $C_1$-$C_6$-alkyl, $C_3$-$C_4$alkenyl, alkyl ($C_1$-$C_4$)-carbonyl or phenyl or $R_1$ and $R_2$ together represent a $C_4$-$C_6$-alkylene chain, whereby the total number of carbon atoms of the radicals $R_1$ and $R_2$ is three or more.

The invention also embraces the salts of these compounds with organic and inorganic acids.

Pyridine-4-carboxylic acid can also be termed isonicotinic acid.

An interesting group of compounds of formula I are those wherein $R_1$ represents $C_1$-$C_3$-alkyl and $R_2$ represents $C_1$-$C_3$-alkyl or phenyl, or $R_1$ and $R_2$ together represent pentamethylene.

Particularly preferred among the above-mentioned compounds are those wherein X represents chlorine.

By alkyl or as alkyl-moiety of another substituent are meant, depending on the number of given carbon atoms, the following groups: methyl, ethyl, propyl, butyl, pentyl or hexyl as well as isomers thereof, such as iso-propyl, iso-, sec.- or tert.-butyl, 1-methylbutyl, isopentyl, 4-methylpent-2-yl etc.

Halogen denotes fluorine, chlorine, bromine or iodine.

The alkylene chains are tetra-, penta- or hexamethylene. By alkenyl are meant allyl and butenyl as well as isomers thereof.

Suitable salt-forming acids are, for example, hydrohalic acids, e.g. hydrochloric acid, hydrobromic acid or hydriodic acid, hydrofluoboric acid, nitric acid, phosphoric acid, thio- or dithiophosphoric acid, sulphuric acid, methanesulphonic acid, acetic acid, haloacetic acids, propionic acid, halopropionic acids, butyric acid, lactic acid, stearic acid, oxalic acid, tartaric acid, maleic acid or benzoic acid.

The compounds of formula I may be produced as follows:

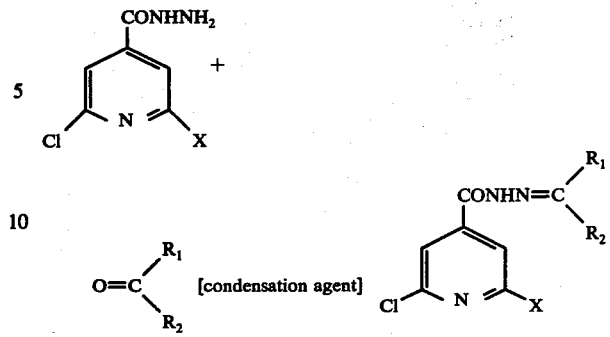

wherein X, $R_1$ and $R_2$ are as defined under formula I.

The aforementioned reaction may be performed in the presence or absence of solvents which are inert to the reactants and which are customarily used in such reactions. Suitable solvents are, for example: alcohols such as methanol or ethanol; ethers such as diethyl ether, dioxane or glyco monomethyl ether, as well as hydrocarbons such as benzene, toluene, petroleum ether, etc.

The remaining reaction conditions also correspond to those of similar known processes, such as the presence or absence of a condensation agent, e.g. triethylamine, N,N-dimethylaniline; temperatures of between 40° and 100° C, preferably between 60° and 80° C; and normal pressure;

The salts may also be produced by methods known per se.

The compounds of formula I can be used for combatting various phytopathogenic microorganisms. In particular, however, they are suitable for controlling phytopathogenic bacteria.

As phytopathogenic bacteria, there can be mentioned, inter alia, members of the genera Pseudomonas, e.g. Pseudomonas tomato, Pseudomonas lachrymans, Pseudomonas phaseolicola, Pseudomonas tabaci and Pseudomonas syringae, Xanthomonas, e.g. Xanthomonas oryzae, Xanthomonas vesicatoria, Xanthomonas phaseoli, Xanthomonas campestri and Xanthomonas citri, as well as Erwinia and Corynebacterium.

A special property of the compounds of formula I is their systemic action against phytopathogenic parasites, i.e. their ability to undergo translocation in a plant to a site of infection that is remote from the point of application. After treatment of the soil, such a compound can thus be absorbed by the roots of a plant and conveyed to the site of infection.

The compounds can be used on useful crops such as cereals, maize, potatoes, rice, vegetables, grape vines, ornamental plants, fruit, and so forth.

In order to adapt them to suit given circumstances and also to broaden their sphere of action, the compounds of formula I can be used together with other suitable pesticides, such as bactericides, fungicides, insecticides or acaricides, or with other active substances influencing plant growth.

The compounds of formula I can be used on their own or together with suitable carriers and/or additives. Suitable carriers and additives may be solid or liquid, and correspond to substances common in formulation practice, such as natural or regenerated mineral substances, solvents, dispersing agents, wetting agents, adhesives, thickeners, binders or fertilisers. Such compositions are produced in a manner known per se by the intimate mixing and grinding of their constituent parts.

For application, the compounds of formula I can be in the following forms:

solid preparations:— dusts, scattering agents, granulates (coated granulates, impregnated granulates and homogeneous granulates) or pellets;

liquid preparations: (a) water-dispersible active-substance concentrates: wettable powders, pastes and emulsions; solution concentrates; (b) solutions: aerosols.

The content of active substance in the above-described compositions is between 0.1 and 95% by weight. The active substances of formula I can be formulated, e.g., as follows:

DUSTS

The following substances are used in the preparation of (a) a 5% dust and (b) a 2% dust:

(a)
5 parts of Active Substance,
95 parts of talcum;

(b)
2 parts of Active Substance,
1 part of highly dispersed silicic acid,
97 parts of talcum.

The active substances are mixed and ground with the carriers and can be applied in this form by dusting.

GRANULATES

The following substances are used to produce a 5% granulate:
5 parts of Active Substance,
0.25 part of epichlorohydrin,
0.25 part of cetyl polyglycol ether,
3.50 parts of polyethylene glycol,
91 parts of kaolin (particle size 0.3 - 0.8 mm).

The active substance is mixed with epichlorohydrin, and the mixture is dissolved in 6 parts of acetone; the polyethylene glycol and cetyl polyglycol ether are then added. The solution obtained in this manner is sprayed onto kaolin and the acetone subsequently evaporated off in vacuo. A microgranulate of this kind is particularly suitable for application to the soil.

WETTABLE POWDERS

The following constituents are used to produce (a) a 70% (b) a 40%, (c) and (d) a 25% and (e) a 10% wettable powder:

(a)
70 parts of Active Substance,
5 parts of sodium dibutyl-naphthalene sulphonate,
3 parts of naphthalenesulphonic acid/phenol-sulphonic acid/formaldehyde condensate 3:2:1,
10 parts of kaolin,
12 parts of Champagne chalk;

(b)
40 parts of Active Substance,
5 parts of sodium lignin sulphonate,
1 part of sodium dibutyl-naphthalene sulphonate,
54 parts of silicic acid;

(c)
25 parts of 2,6-dichloropyridine-4-carboxylic acid-2-butyliden-hydrazon,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin;

(d)
25 parts of Active Substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;

(e)
10 parts of Active Substance,
3 parts of a mixture of the sodium salts of saturated fatty alcohol sulphates,
5 parts of naphthalenesulphonic acid/formaldehyde condensate,
82 parts of kaolin.

The active substances are intimately mixed in suitable mixers with the additives, and the mixture is then ground in appropriate mills and rollers. Wettable powders are obtained having excellent wetting and suspension properties, which powders can be diluted with water to give suspensions of the desired concentration and which can be used, in particular, for leaf application.

EMULSIFIABLE CONCENTRATES

The following substances are used to produce a 25% emulsifiable concentrate:
25 parts of Active Substance,
2.5 parts of epoxidised vegetable oil,
10 parts of an alkylarylsulphonate/fatty alcohol polyglycol ether mixture,
5 parts of dimethylformamide,
57.5 parts of xylene.

It is possible to produce from this concentrate, by dilution with water, emulsions of the desired concentration, which are particularly suitable for leaf application.

The following Examples serve to further illustrate the invention without limiting the scope thereof. Temperature values are given in degrees Centigrade.

EXAMPLE 1 (COMPOUND NO. 1.10)

Production of 2,6-dichloropyridine-4-carboxylic acid-2'-butylidene-hydrazone of the formula

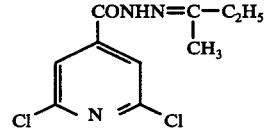

20.6 g of 2,6-dichloropyridine-4-carboxylic acid-hydrazide were refluxed with
25 ml of methyl ethyl ketone and 100 ml of ethanol for 2 hours. The reaction product crystallised out on cooling. It was filtered off with suction and washed with a small amount of ethanol to give colourless crystals, m.p. 140°–143°.

The following compounds were produced in an analogous manner and/or by one of the methods described herein:

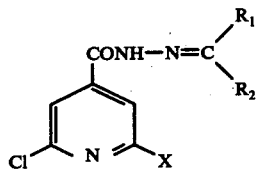

| Comp. No. | X | R₁ | R₂ | Physical data |
|---|---|---|---|---|
| 1.11 | Cl | H | —CH=\ CH—CH₃ | m.p. 197–200° |
| 1.12 | Cl | —CH₃ | —ₙC₃H₇ | m.p. 114–116° |
| 1.13 | Cl | —CH₃ | —CH=C(CH₃)₂ | m.p. 138–142° |
| 1.14 | Cl | H | —ᵢC₃H₇ | m.p. 190–194° |
| 1.15 | Cl | —CH₃ | —COCH₃ | m.p. 188–191° |
| 1.16 | Cl | —C₂H₅ | —C₆H₅ | m.p. 160–162° |
| 1.17 | Cl | H | —C₆H₅ | m.p. 233–235° |
| 1.18 | Cl | —(CH₂)₅— | | m.p. 179–181° |
| 1.19 | Cl | CH₃ | —C₆H₅ | m.p. 203–206° |
| 1.20 | CH₃ | H | —CH=\ CH—CH₃ | m.p. 182–184° |
| 1.21 | CH₃ | H | —CH₃ | m.p. 149–152° |
| 1.22 | Cl | H | —ₙC₃H₇ | m.p. 182–184° |
| 1.23 | Cl | —(CH₂)₄— | | m.p. 182–185° |
| 1.24 | Cl | —(CH₂)₆— | | m.p. 154–156° |
| 1.25 | Cl | —CH₃ | —ᵢC₄H₉ | m.p. 129–131° |
| 1.26 | Cl | n-C₃H₇ | —C₆H₅ | m.p. 144–146° |

EXAMPLE 4

Action against *Pseudomonas lachrymans* on cucumbers and against *Xanthomonas vesicatoria* on paprika:

a. Residual Action (R)

Young cucumber and paprika plants were sprayed until dripping wet with the active substance in the form of a spray liquor with a content of active substance of 1000 ppm. One day after this application, the plants were infested by spraying of the underside of the primary leaves with suspensions of the respective bacteria, and then incubated for 8 days at 22° C with 95% relative humidity. An evaluation was made after this period of time on the basis of the number of typical disease spots.

b. Systemic Action (S)

Young cucumber and paprika plants were watered with the active substance in the form of a suspension of the active substance (concentration 100 ppm relative to the pot soil). One day after this application, the plants were infested by spraying of the underside of the primary leaves with suspensions of the respective bacteria, and incubation was subsequently carried out for 8 days at 22° C with 95% relative humidity. After this period of time, the evaluation was made on the basis of the number of typical disease spots.

The following pyridine-4-carboxylic acid derivatives exhibited in the case of the stated bacteria a good action (i.e. plants less than 20 % infested compared with untreated but infested control plants).

| Compound No. | Pseudomonas lachrymans | | Xanthomonas vesicatoria | |
|---|---|---|---|---|
| | R | S | R | S |
| 1.10 | + | + | + | + |
| 1.11 | + | + | + | |
| 1.12 | + | + | + | + |
| 1.13 | + | + | + | |
| 1.14 | + | + | + | |
| 1.15 | + | + | + | |
| 1.16 | + | + | + | + |
| 1.17 | + | + | + | + |
| 1.18 | + | + | + | |
| 1.19 | + | + | + | + |
| 1.20 | + | + | | + |
| 1.21 | + | + | | + |
| 1.22 | | | + | + |
| 1.23 | | | + | + |

We claim:
1. A compound of formula I

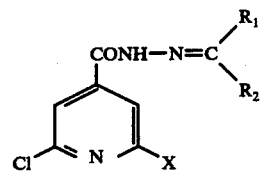

wherein
X represents chlorine, methyl or methoxy
R₁ represents hydrogen or C₁-C₆-alkyl, and
R₂ represents C₁-C₆-alkyl, C₃-C₄-alkenyl, alkyl(C₁-C₄)-carbonyl or phenyl, or
R₁ and R₂ together represent a C₄-C₆-alkylene chain, whereby the total number of carbon atoms of the radicals R₁ and R₂ is three or more as well as the microbicidally effective acid addition salts thereof.

2. A compound of the formula I as claimed in claim 1 wherein R₁ represents C₁-C₃-alkyl and R₂ represents C₁-C₃-alkyl or phenyl or R₂ and R₃ together represent pentamethylene.

3. A compound of the formula I as claimed in claim 1 wherein X represents chlorine.

4. A compound of the formula I as claimed in claim 2 wherein X represents chlorine.

5. A compound according to claim 1 which is 2,6-dichloropyridine-4-carboxylic acid-2'-pentylidene hydrazone of the formula

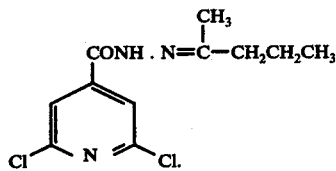

6. A compound according to claim 1 which is 2,6-dichloropyridine-4-carboxylic acid-1'-phenylprop(1'-)ylidene-hydrazone of the formula

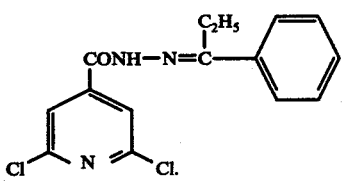

7. A compound according to claim 1 which is 2,6-dichloropyridine-4-carboxylic acid-cyclohexylidene-hydrazone of the formula

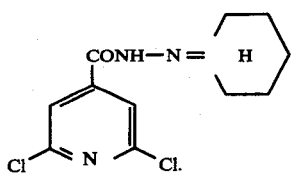

8. A microbicidal composition comprising as active substance a microbicidally effective amount of a compound as claimed in claim 1 together with a suitable carrier therefor.

9. A microbicidal composition comprising as active substance a microbicidally effective amount of a compound as claimed in claim 3 together with a suitable carrier therefor.

10. A microbicidal composition comprising as active substance a microbicidally effective amount of a compound as claimed in claim 4 together with a suitable carrier therefor.

11. A microbicidal composition comprising as active substance a microbicidally effective amount of a compound as claimed in claim 5 together with a suitable carrier therefor.

12. A microbicidal composition comprising as active substance a microbicidally effective amount of a compound as claimed in claim 6 together with a suitable carrier therefor.

13. A microbicidal composition comprising as active substance a microbicidally effective amount of a compound as claimed in claim 7 together with a suitable carrier therefor.

14. A microbicidal composition comprising as active substance a microbicidally effective amount of a compound as claimed in claim 8 together with a suitable carrier therefor.

15. A method for combatting phytopathogenic microorganisms which comprises applying thereto or to the locus thereof a microbicidally effective amount of a compound as claimed in claim 1.

16. A method for combatting phytopathogenic microorganisms which comprises applying thereto or to the locus thereof a microbicidally effective amount of a compound as claimed in claim 2.

17. A method for combatting phytopathogenic microorganisms which comprises applying thereto or to the locus thereof a microbicidally effective amount of a compound as claimed in claim 3.

18. A method for combatting phytopathogenic microorganisms which comprises applying thereto or to the locus thereof a microbicidally effective amount of a compound as claimed in claim 4.

19. A method for combatting phytopathogenic microorganisms which comprises applying thereto or to the locus thereof a microbicidally effective amount of a compound as claimed in claim 5.

20. A method for combatting phytopathogenic microorganisms which comprises applying thereto or to the locus thereof a microbicidally effective amount of a compound as claimed in claim 6.

21. A method for combatting phytopathogenic microorganisms which comprises applying thereto or to the locus thereof a microbicidally effective amount of a compound as claimed in claim 7.

22. A method as claimed in claim 15 wherein the microorganisms to be combatted are phytopathogenic bacteria.

23. A method as claimed in claim 16 wherein the microorganisms to be combatted are phytopathogenic bacteria.

24. A method as claimed in claim 17 wherein the microorganisms to be combatted are phytopathogenic bacteria.

25. A method as claimed in claim 18 wherein the microorganisms to be combatted are phytopathogenic bacteria.

26. A method as claimed in claim 19 wherein the microorganisms to be combatted are phytopathogenic bacteria.

27. A method as claimed in claim 20 wherein the microorganisms to be combatted are phytopathogenic bacteria.

28. A method as claimed in claim 21 wherein the microorganisms to be combatted are phytopathogenic bacteria.

* * * * *